United States Patent [19]

Schadrack, III et al.

[11] Patent Number: 4,549,538
[45] Date of Patent: Oct. 29, 1985

[54] PIN INSERTER SHEATH

[75] Inventors: William C. Schadrack, III, Memphis, Tenn.; Robert W. McQueen, Warsaw, Ind.; Joyce K. Eyerly, White Bear Lake, Minn.

[73] Assignee: Zimmer, Inc., Warsaw, Ind.

[21] Appl. No.: 441,199

[22] Filed: Nov. 12, 1982

[51] Int. Cl.[4] .............................................. A61F 5/04
[52] U.S. Cl. ............................ 128/92 EB; 128/92 C; 128/303 R; 623/16; 623/66
[58] Field of Search .............. 128/92 EB, 419 F, 82.1, 128/305.1, 303 R, 303.1, 83; 3/1.9, 1

[56] References Cited

U.S. PATENT DOCUMENTS

| | | | |
|---|---|---|---|
| 1,308,798 | 7/1919 | Masland | 128/305.1 |
| 2,811,969 | 11/1957 | Shubert | 128/303 R |
| 3,128,768 | 4/1964 | Geistauts | 128/83 |
| 3,384,085 | 5/1968 | Hall | 128/305.1 |
| 3,835,858 | 9/1974 | Hagen | 128/305 |
| 3,865,113 | 2/1975 | Sharon et al. | 128/305 |
| 4,154,248 | 5/1979 | Jones | 128/419 |
| 4,279,552 | 7/1981 | Epstein | 408/112 |
| 4,425,115 | 1/1984 | Wuchinich | 128/303 R |

OTHER PUBLICATIONS

Zimmer Brochure, "The Alternate Treatment of Fracture Nonunion", Lit. No. B-2360-1, C, 1979, Zimmer USA, Inc.

Primary Examiner—Richard J. Apley
Assistant Examiner—David Isabella
Attorney, Agent, or Firm—Margaret L. Geringer

[57] ABSTRACT

A pin inserter sheath which consists of a plurality of telescoping tubular portions. The sheath is adapted for attachment to a drilling device. A channel extends throughout the elongated telescoping tubular portion which is substantially adapted to the shape of the pin being inserted. The conforming channel provides lateral support to the pin therefore minimizing inflections in the pin as it is being drilled.

5 Claims, 8 Drawing Figures

PIN INSERTER SHEATH

BACKGROUND OF THE INVENTION

The present invention generally relates to pin inserting guides, and more particularly, to guides for inserting thin, flexible, elongated pins.

Orthopaedic surgeons frequently find it necessary to insert elongated, thin cathode pins. These pins are introduced percutaneously and through a portion of bone, such that the exposed tip of the pin comes to rest directly in the non-union site of a fracture. The introduction of such cathode pins is known in the art. These cathode pins are typically utilized in conjunction with a particular method of electrical bone growth stimulation. This method is more particularly described in a Zimmer, Inc. brochure entitled, "The Alternate Treatment of Fracture Nonunion, Electrical Stimulation to Induce Osteogenesis." This brochure is identified as Zimmer Literature No. B-2360-1 © 1979.

The cathode pins which are utilized are very thin, elongated stainless steel pins. The pins are insulated with a thin Teflon ® coating of approximately 0.001 inch, which covers the entire length of the pin except for both the extreme distal tip portion and the extreme proximal end portion. The distal tip portion includes a sharp end point for penetration into the bone.

The thin, elongated cathode pins are flexible and easily bendable, and consequently, when they are attached to a drilling device, and drilled into the body, they are subject to various inflections, bending, etc. A prior art Cathode Pin Inserter has been used in conjunction with a hand-operated drill to facilitate the percutaneous insertion of these cathode pins. This prior art device is illustrated end described on pages 8 through 11 of the above-referenced literature No. B-2360-1 and is identified as Product No. 5012-04.

This inserter consists of a stabilizer metal bar mechanism which holds a thin plastic tube in place. The stabilizing mechanism is attached to a suitable drilling device. The pin is positioned in and extends from the chuck of the drilling device. The stabilizing mechanism supports the elongated plastic tube which is positioned in alignment with the pin, such that the mid-portion of the pin can be inserted through a small channel in the plastic tube, hence partially stabilizing the pin. Approximately 1 to 1½ inches of the cathode pin projects from the end of the plastic tube support. If additional pin length is required, the stabilizing bar can be retracted toward the chuck and drill by loosening a bolt, sliding a moveable bar portion and retightening the bolt. If still more pin length is required for insertion, the plastic guide tube can be unscrewed and repositioned and potentially removed. This inserter involves time-consuming positioning of parts, and readjustment of parts in order to insert additional length of pin.

While the prior art inserter device described above is currently used with a hand-operated drill, this type of inserter could be adapted for use with a power instrument.

OBJECTS OF THE INVENTION

A principle object of the invention is to provide a pin inserting sheath which conforms to the shape of the pin being inserted so as to provide lateral support in order to minimize inflections of the pin upon insertion.

Another object of the invention is to provide a pin inserting sheath which acts as a telescoping support with the sheath collapsing as the pin is inserted.

A further object of the invention is to provide such a telescoping sheath which is simple to attach to a suitable drilling device and easy to use for pin insertion.

A still further object of the invention is to provide a pin inserting sheath which is inexpensive to manufacture and which may be disposable.

A further object of the invention is to provide a pin inserting sheath which is suitable for the insertion of pins with a power tool.

A further object of the invention is to provide a pin inserter sheath which is suitable for use with the TEFLON coated cathode pins previously described for use with an electrical bone growth stimulation system, and which will prevent marring or scratching of the insulating TEFLON coating.

SUMMARY OF THE INVENTION

The present invention accomplishes all of the above objects of invention. The present invention provides a pin inserting sheath which consists of a plurality of telescoping tubular portions, each portion sequentially smaller in outside diameter than the previous portion as the sheath progresses from the proximal to the distal end.

The sheath may be made out of any suitable material. A particularly advantageous material suitable for use for inserting certain thin elongated cathode pins, is plastic. This allows the sheath to be lightweight, easy to manufacture, as well as enabling the sheath to be molded.

The sheath is adapted to allow for quick and easy attachment to a suitable drilling device. In one embodiment the attachment means allows for a snap-on attachment in which the proximal sheath includes a portion which snaps onto the drilling device.

BRIEF DESCRIPTION OF THE DRAWINGS

These features and objects of the invention, as well as other, will become apparent to those skilled in the art by referring to the accompanying drawings in which.

DETAILED DESCRIPTION OF THE INVENTION

Figure 1:
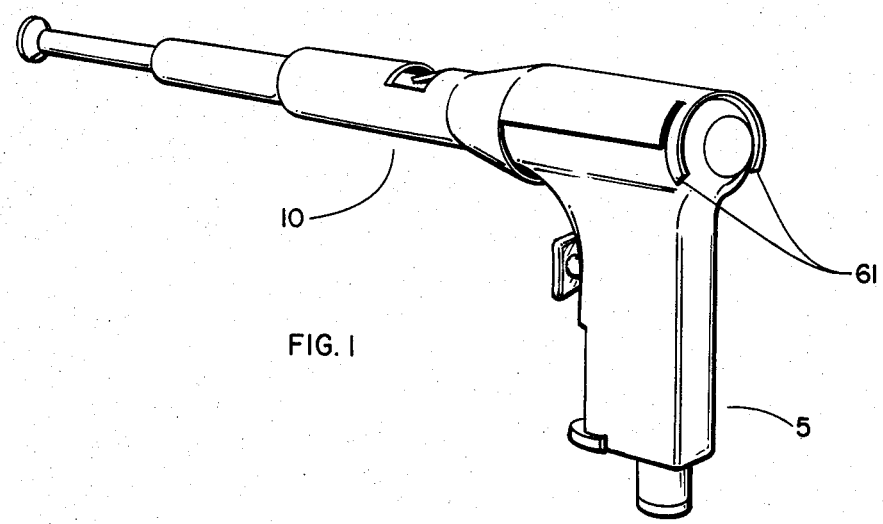
FIG. 1 is a pictorial view of a particularly advantageous embodiment of the pin inserter sheath in accordance with the present invention shown attached to a suitable drilling device.

FIGS. 1-8 illustrate a particularly advantageous embodiment of the pin inserter sheath 10 according to this invention.

The pin inserter sheath 10 is comprised of a plurality of telescoping tubular portions. The sheath 10 includes a fixed portion 20 adapted for attachment to a drilling device and at least one slideable, retractable portion 40. In the embodiment illustrated, the sheath 10 is comprised of three telescoping tubular portions: the fixed rear body portion 20; a retractable middle body portion 30; and a retractable front body portion 40. The body portions each successively decrease in outside diameter moving from the largest rear portion 20 to the slightly smaller middle portion 30 to the smallest front portion 40 to permit telescoping of the front into the middle, and then both into the rear portion. A continuous channel 22, 32, and 42 is provided which extends throughout the rear portion 20, middle portion 30, and front portion 40 respectfully. The channel portion 42 is dimensioned so as to conform to the external shape of a pin such as the cathode pin 50 shown in FIG. 8, so as to provide lateral support to the pin. This lateral support minimizes inflections in the pin 50 as it is being drilled caused by application of force through the pin to the bone. An outlet 45 is provided at the most distal end of the front body portion 40, to enable the pin 50 to extend from the continuous connecting channel portion 42.

Figure 8:
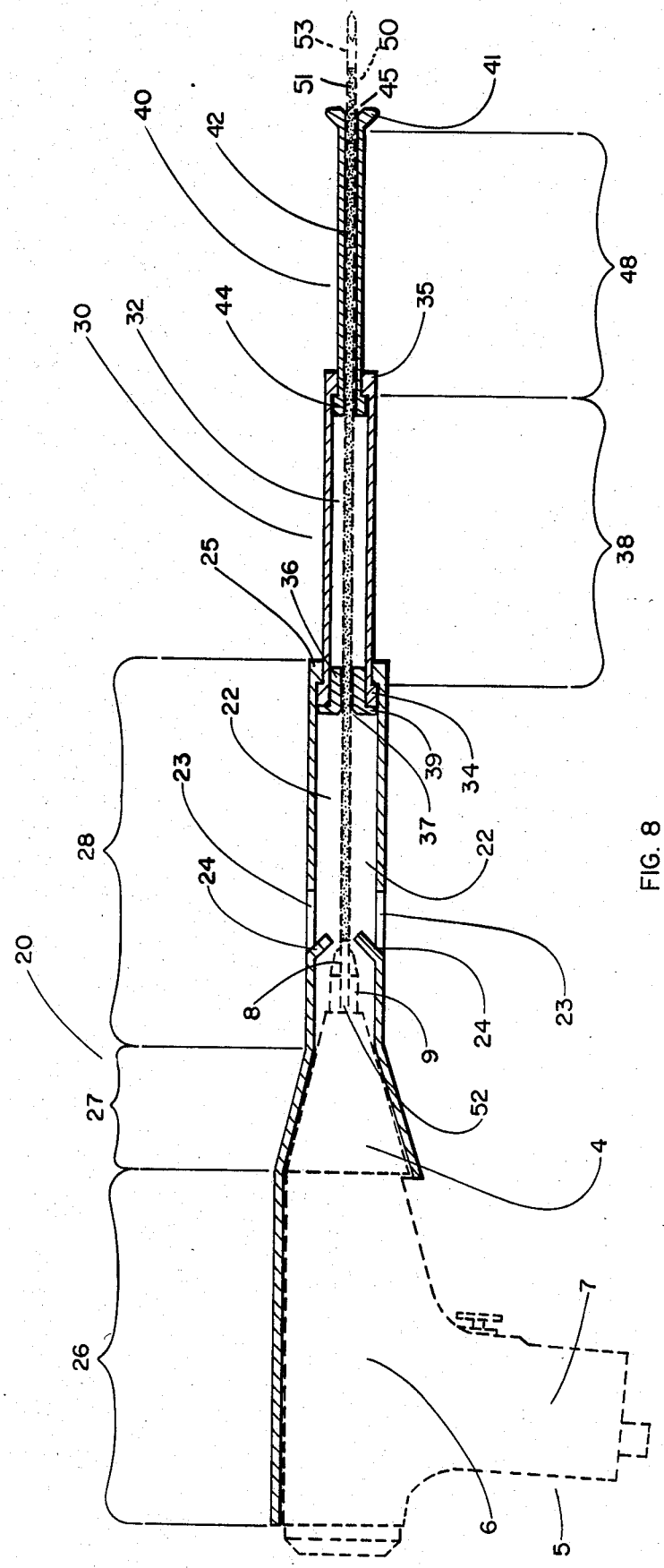
FIG. 8 is an enlarged cross-sectional view of the pin inserter sheath shown attached to a suitable drilling device, and shown with a suitable cathode pin device inserter through the sheath and attached to the drilling device.

The rear body portion 20 is comprised of a stepped configuration including an enlarged proximal portion 26, a tapering section 27, and an elongated thinner portion 28. The enlarged proximal portion 26 is adapted to be snap-fit onto a particular drilling device 5, as shown in FIGS. 1 and 8. The drilling device 5 has a somewhat cylindrical upper body 6 attached to a handle portion 7. To enable this snap-fit attachment, the proximal portion 26 is adapted to the cylindrical body shape 6 of the drilling device 5, and the tapered portion 27 tapers or conforms about the tapered front 4 of the drilling device 5. The proximal portion 26 includes a cut-out portion 29 which facilitates a secure attachment to the drilling device 5. The proximal portion 26 further includes, at its most rearward end, a thin slot 60 extending partially around the proximal portion 26 and a thin extended securing ring 61. The securing ring 61 does not extend around to become a fully closed ring, but provides a gap 62 in the ring 61 which enables the ring to snap securely onto the drilling device 5. The gap 62 enables the thin ring 61 to expand slightly to snap over the drilling device 5 and then spring back to its natural shape to lock the sheath 10 onto the drilling device.

The ring 61, as shown in FIG. 1, may be located so that upon snapping onto the device 5, the ring 61 is proximal to the handle 7, and fits securely around the most proximal cylindrical portion of the upper body 6. This securing ring 61, in combination with the previously described conforming snap-fit shape of the remaining proximal portion 26, and conforming shape of the tapering section 27 affords a tight fitting enclosure about the drilling device 5 when mounted thereon. It is understood that the sheath 10 could be adapted to conform to other suitable drilling devices.

The elongated thinner portion 28 of the rear body portion 20 retains concentrically therewithin the enlarged flange 34 of the middle body portion 30. The enlarged flange 34, which is restrained longitudinally from forward movement by ledge 25, prevents the middle body 30 from slipping through the open distal end of the rear body portion 20. The close fit of the outer diameter of flange 34 with the inner diameter of the distal portion of channel 22 provides circumferential support.

The flange 34 is integrally connected to an elongated tubular portion 38. This elongated portion 38 has a smaller outer diameter than that of the elongated thinner portion 28 of the rear body 20. The outer diameter of the elongated portion 38 is just slightly smaller than the inner diameter of the opening at the distal end of the rear body 20. The distal portion of the channel 32 of the middle body 30 includes an aligning plug 36 which press fits into the channel 32. The plug 36 includes an aligning channel 37 which enables the channels 32 and 33 of the middle and rear portions to be continuously connected without interruption. The aligning channel 37 is dimensioned so that the proximal end of the pin 50 fits snugly therein. The plug 36 further includes a flange 39 to prevent the plug 36 from being pushed too far into the middle body channel 32.

The middle body 30 further includes a restraining ledge 35 at its distal end which retains the enlarged flange 44 of the front body portion 40. The enlarged flange 44 prevents the front body 40 from slipping through the open distal end of the middle body portion 30. The close fit of the outer diameter of flange 44 with the inner diameter of the distal portion of channel 32 provides circumferential support.

The flange 44 is integrally connected to an elongated tubular portion 48 having a smaller outer diameter than that of the elongated tubular portion 38 of the middle body 30. The outer diameter of the elongated portion 48 is just slightly smaller than the inner diameter opening at the distal end of the middle body 30. The inner channel 42 of the front body 40 has a uniform diameter throughout its length which opens directly into the middle body channel 32 at the proximal end of the front body 30 and which terminates in a channel outlet 45 at the distal end of the front body 40. The outlet 45 enables the pin 50 to extend out from the channel 42.

The uniformly diametered channel 42 has the same diameter of the aligning channel 37 of the aligning plug 36. Therefore, the diameter of channel 42 is also just slightly larger than the diameter of the pin 50 to permit a snug fit upon insertion therein. This allows for only minimal clearance between the channels 42 and 37 and the outer diameter of the pin 50 in order to provide strong lateral support to the pin 50. The channel 42 is in linear alignment with the aligning channel 37 and further with the chuck opening 8 of the drilling device 5. The channels 42 and 37 which align the pin 50 and which conform to the outer diameter of the pin 50 provide lateral support for the pin 50 as it is being inserted which minimizes inflections or bending of the thin pin 50 during drilling.

The front body 40 further includes an enlarged abutment flange 41 which protrudes from the outer diameter of the most distal end of the front body 40. The abutment portion 41 is for placement against the object, such as a human body in the case of a flexible cathode pin 50, into which a pin 50 is to be drilled or inserted. The abutment portion 41 illustrated has a circular flat front face, and it acts as a stable end in contact to the skin, or other drilling surface.

Figure 2:
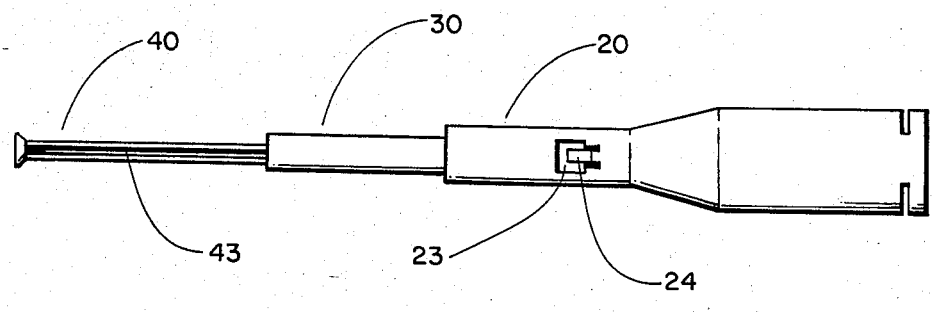
FIG. 2 is a top view of the pin inserter sheath of FIG. 1.
Figure 3:
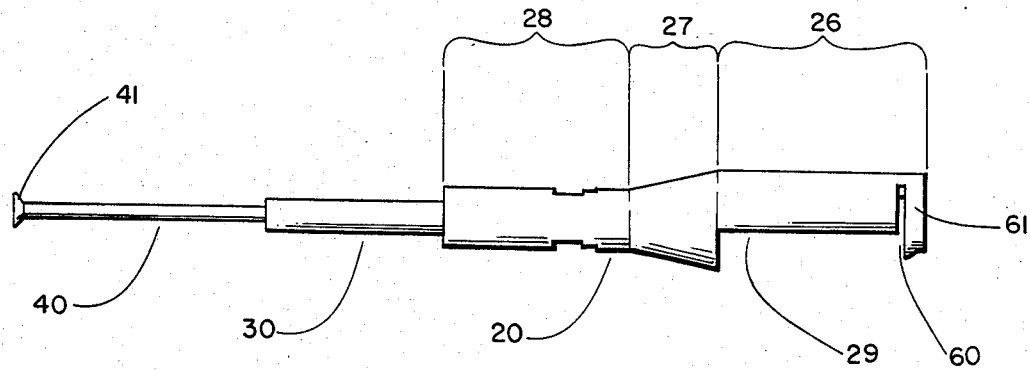
FIG. 3 is a side view of the pin inserter sheath of FIG. 1.
Figure 4:
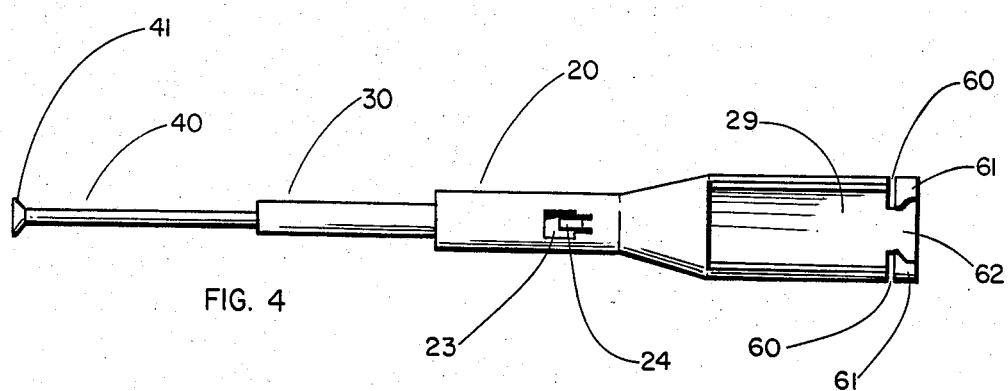
FIG. 4 is a bottom view of the pin inserter sheath of FIG. 1.
Figure 5:
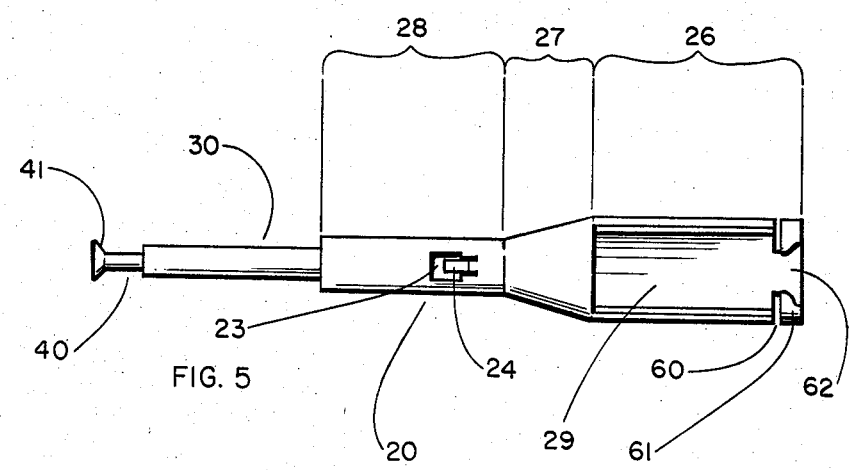
FIG. 5 is a bottom view of the pin inserter of FIG. 4 shown in a partially collapsed position.
Figure 7:
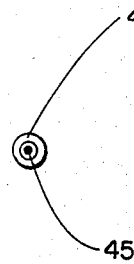
FIG. 7 is a front end view of the inserter of FIG. 6.

The front body 40 also may include an elongated cutaway section 43 along the length of the elongated tubular portion 48, as illustrated in FIG. 2. The elongated cutaway section 43 is primarily for the convenience of molding and assembly. The orientation of the cutaway section may vary because the elongated telescoping tubular portions 40 and 30 are not only retractable, but are freely rotatable relative to one another. The cutaway section 43 exposes the channel 42 in which the pin 50 lies.

The rear body portion 30 may include a window portion 23. The embodiment illustrated, shows two window openings 23 each oppositely positioned from the other. The windows are positioned at about the area where the chuck 9 of the drilling device or pin driver 5 is located. These viewing windows 23 aid the user in positioning the cathode pin 5 into the chuck 9. A tab 24 is provided in each window 23 which projects inwardly into the rear body channel 22. The inwardly bent tabs 24 prevent the telescoping front and middle bodies 40 and 30 from falling out of the rear body portion 20.

An alternative to the windows 23 in the rear body 20 is to have the sheath 10 made of clear material which enables the user to see the pin 50 through the sheath 10.

Preferably, each of the individual components of the sheath assembly 10 is molded from a lightweight plastic material. The sheath 10 is advantageously assembled in the following manner. The front body 40 is inserted through the middle body 30. The protruding abutment portion 41 is then press fit onto the distal tip of the front body 40. The aligning plug 36 is press fit into the proximal end of the channel 32 of the middle body 30. The middle and front bodies 30 and 40 are then inserted in through the rear body 20, and the tabs 24 are subsequently stacked or bent inward into the channel 22 of the rear body 20, thereby preventing the front and middle bodies 40 and 30 from falling out of the sheath through the rear body portion 20.

To utilize the pin inserting sheath 10, the sheath 10 is snapped securely onto a suitable drilling device 5. This is done by sliding the sheath 10 onto the front (distal portion) of the drilling device 5 to allow the tapering portion 27 of the sheath 10 to accept the tapering front portion of the drilling device, and pushing on the proximal portion of the sheath 10 until it snaps into place. A cathode pin 50 is then ready for insertion into the sheath 10. The cathode pin 50 includes a TEFLON coating which acts as an insulating material. The proximal portion 52 of the pin 50 is uncoated. This uncoated proximal portion 52 is the portion of the pin 50 which will be engaged in the chuck 9 of the drilling device 5. The distal tip 53 of the pin is also uncoated. The distal tip 53 incorporates a sharpened drilling tip and is uncoated to conduct the current used in the electrical bone growth stimulation system to the fracture site. The cathde pins 50 are to be drilled through skin and bone such that the uncoated distal tip 53 will come to rest directly in the bone fracture site.

The proximal end 52 of the pin 50 is inserted through the outlet 45 in the front body 40. As insertion proceeds, the pin is inserted through front channel 42 and into middle channel 32. The pin 50 then proceeds through the aligning channel 37 and into the rear channel 22. By viewing through the windows 23, the proximal end 52 of the pin 50 is inserted into the opening of the driver chuck 9 until the TEFLON insulation of the pin is approximately flush with the distal end of the driver chuck 9. The insulating TEFLON coating should not be inserted into the chuck portion 9 of the driver 5, as the insulation may damage the driver. It is also important that the insulated cathode pin 50 be gripped on its uncoated proximal end 52 so as not to mar or scratch the insulating TEFLON coating. The plastic material of the sheath is also advantageous for preventing marring or scratching of the insulating coating on the pin 50.

Figure 6:
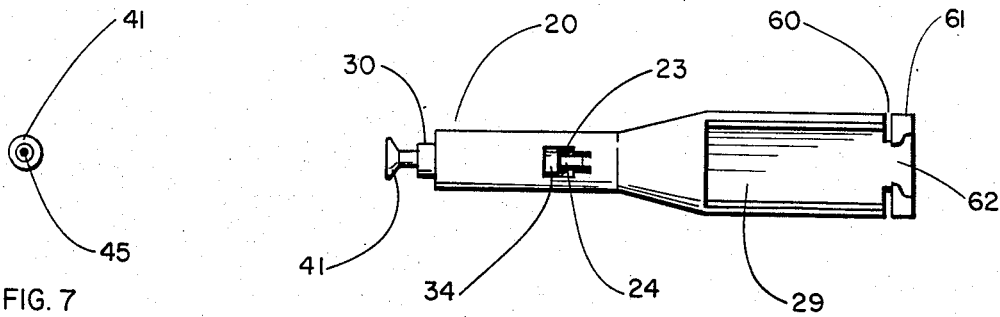
FIG. 6 is a bottom view of the pin inserter of FIG. 4 shown in a fully collapsed position.

It is noted that the pin 50 may be inserted while the sheath 10 is collapsed as shown in FIG. 6. In the collapsed position, front channel 42, aligning channel 37 and the entrance to the chuck 9 are in close alignment for inserting the pin through the sheath 10 and into the chuck 9. The front and middle bodies 40 and 30 could then be manually extended to the fully extended position (as in FIG. 8) for the proper position to begin insertion.

The drill chuck 9 preferably clamps onto the cathode pin 50 when an external trigger on the driver 5 is pulled. Release of the trigger will release the chuck's grip on the pin 50, and allow free movement of the pin 50 in the wire driver chuck 9. The user should periodically check the cathode pin position in the chuck 9 to ensure proper positioning.

Now the pin 50 is ready for insertion. The distal tip 53 of the pin 50 is placed against the skin and the drilling may begin. The sheath 10 is particularly suitable for power drilling. In using the present inserter sheath invention with a power drill, one hand controls the power instrument, and the other hand is free to help guide and support the telescoping mechanism. While the present invention could be adapted for use with a hand operated drilling device, it would not be as desirable because one hand must hold and support the drill, while the other hand turns the handle or crank.

As the drilling proceeds, the distal end 53 of the pin 50 penetrates the body. Soon the abutment portion 41 engages the skin. As drilling continues, the front portion 40 of the sheath 10 will automatically begin to retract into the enlarged portion of channel 32 of the middle body 30. If additional pin length is required, the front and middle sections 40 and 30 may further retract into the enlarged rear body channel 22. The front channel 42 in conjunction with the alignment channel 37 provides a close fit with the pin and is continually giving lateral support to the pin 50, hence stabilizing the pin during insertion and preventing bending and inflections of the pin 50 which without this lateral support, would occur due to the elongated very thin, flexible configuration of the cathode pins 50. The telescoping sections of the inserter 10 automatically adjust to the decreasing pin length as the pin 50 is inserted, which, in turn, reduces the possibility of a whipping action during insertion.

When the pin 50 is inserted to the desired depth, the trigger on the drilling device 5 is released, releasing the grip of the chuck 9 on the pin 50. The sheath 10 is then easily pulled off the proximal portion of the pin 50. To remove the sheath 10, simply pull up and forward on the proximal portion of the sheath 10.

The inserter sheath 10 may be packaged for use in a presterilized condition. Suitable sterilization, such as gamma irradiation, may be used.

While the present pin inserter sheath invention has been described in terms of its preferred embodiment, with reference to use with a cathode pin and for use in a particular electronic bone growth stimulation system, it is understood that the sheath design could be adapted for use with other pins, wires, or drill bits requiring stabilization upon insertion. The present sheath is very simple to use, and accomplishes the desired pin stabilization in a simple fashion. The desired length of pin may be inserted as the sheath automatically retracts as needed; hence, eliminating the cumbersome problems associated with the prior art device previously discussed. The present sheath 10 also is suitable for power drilling of pins 50.

The invention described herein is a collapsable pin inserting sheath comprised of a plurality of telescoping tubular portions. The tubular portions are able to retract into one another as the pin is inserted. The sheath provides lateral support to the pin, therefore minimizing inflections as the pin is being drilled. While this invention has been described and exemplified in terms of a particularly advantageous embodiment, those skilled in the art can appreciate that modifications can be made without departing from the spirit and scope of this invention.

We claim:

1. A pin inserter sheath for attachment to a pin drilling device, the device including a main body and a handle attached thereto, said sheath comprising:
   (a) a proximal portion adapted for attachment to the pin drilling device; and
   (b) at least one member attached to said proximal portion and having a channel therethrough for receiving a pin therein, and for providing lateral support to at least a portion of the received pin, said member having an outlet continuous with said channel for protrusion of the pin therefrom, said member being retractable into said proximal portion and slideable along said pin while providing lateral support, and wherein said proximal portion includes a means for securing the sheath externally onto the body of the drilling device, said means including an elongated stabilizing portion which extends substantially over the upper portion of the main body of the drilling device and further attached to the drilling device by a thin, extended securing ring, said ring including a gap in the ring enabling the ring to snap securely about the proximal end of the main body of the drilling device.

2. A pin inserter sheath as described in claim 1 having a plurality of members including a middle member attached to and retractable into said proximal portion, and a distal member attached to and retractable into said middle member, said distal member providing said lateral support, and said channel extending continuously through said members when in an unretracted position.

3. A pin inserter sheath as described in claim 1 wherein said member includes an enlarged abutment portion forming a solid, flat front face surrounding said outlet, said face to be placed against the object into which the pin is drilled.

4. A pin inserter sheath as described in claim 1; wherein said proximal portion includes a pin positioning viewing window means which enables the pin receiving portion of the drilling device to be visible through the window means to aid in positioning the pin in the drilling device.

5. A pin inserter sheath comprising:
   (a) a proximal portion adapted for attachment to a pin drilling device; and
   (b) a plurality of members including a middle member attached to and retractable into said proximal portion, and a distal member attached to and retractable into said middle member, said members having a channel extending continuously therethrough for receiving a pin therein, and said distal member providing lateral support to at least a portion of the received pin, and having an outlet continuous with said channel for protrusion of the pin therefrom, said distal member being slideable along said pin while providing lateral support, and wherein said proximal portion includes a cut-out window portion for viewing to aid in positioning the pin in the drilling device, and wherein said proximal portion includes a tab which is bent inward at the window portion into the channel opening to prevent the distal and middle members from falling out of the proximal portion.

* * * * *